US012668822B2

(12) United States Patent (10) Patent No.: US 12,668,822 B2
Hooe et al. (45) Date of Patent: Jun. 30, 2026

(54) MULTI-MECHANISTIC CHANNELING WITHIN A BIOCATALYTIC CASCADE FOR THE PRODUCTION OF 1,3-DIAMINOPROPANE

(71) Applicant: The Government of the United States of America, as represented by the Secretary of the Navy, Arlington, VA (US)

(72) Inventors: Shelby L. Hooe, Washington, DC (US); Igor L. Medintz, Washington, DC (US); Gregory A. Ellis, Washington, DC (US); Kimihiro Susumu, Hanover, MD (US); Tanya Tschirhart, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 244 days.

(21) Appl. No.: 18/674,484

(22) Filed: May 24, 2024

(65) Prior Publication Data

US 2025/0146034 A1 May 8, 2025

Related U.S. Application Data

(60) Provisional application No. 63/503,983, filed on May 24, 2023.

(51) Int. Cl.
*C12P 13/00* (2006.01)
*B01J 31/00* (2006.01)
*B01J 35/45* (2024.01)
*B82Y 30/00* (2011.01)
*B82Y 40/00* (2011.01)
*C12N 9/02* (2006.01)
*C12N 9/10* (2006.01)
*C12N 9/12* (2006.01)
*C12N 9/88* (2006.01)
*C12N 11/18* (2006.01)
*C12P 5/02* (2006.01)

(52) U.S. Cl.
CPC ........... *C12P 13/001* (2013.01); *B01J 31/003* (2013.01); *B01J 35/45* (2024.01); *C12N 9/0008* (2013.01); *C12N 9/1096* (2013.01); *C12N 9/1217* (2013.01); *C12N 9/88* (2013.01); *C12N 11/18* (2013.01); *C12P 5/02* (2013.01); *C12Y 102/01011* (2013.01); *C12Y 206/01076* (2013.01); *C12Y 207/02004* (2013.01); *C12Y 401/01086* (2013.01); *C12Y 403/01001* (2013.01); *B82Y 30/00* (2013.01); *B82Y 40/00* (2013.01)

(58) Field of Classification Search
CPC ......... C12P 13/001; C12P 5/02; B01J 31/003; B01J 35/45; C12N 9/0008; C12N 9/1096;

C12N 9/1217; C12N 9/88; C12N 11/18; C12N 9/0006; C12Y 102/01011; C12Y 206/01076; C12Y 207/02004; C12Y 401/01086; C12Y 403/01001; B82Y 30/00; B82Y 40/00

See application file for complete search history.

(56) References Cited

PUBLICATIONS

Kummer, M.J., Lee, Y.S., Yuam, M., Alkotaini, B., Zhai, J., Blumenthal E., and Minteer, S.D. (2021). "Substrate Channeling by a Rationally Designed Fusion Protein in a Biocatalytic Cascade." JACS Au 1(8): 1187-1197.

Hooe, S., Breger, J., Dean, S., Susumu, K., Oh, E., Walper, S., Ellis, G.A., and Medintz, I.L. (2022). "Benzaldehyde Lyase Kinetic Improvements, Potential Channeling to Alcohol Dehydrogenase, and Substrate Scope when Immobilized on Semiconductor Quantum Dots." ACS Appl. Nano Mater. 5(8): 10900-10911.

Díaz, S.A., Choo, P., Oh, E., Susumu, K., Klein, W.P., Walper, S.A., Hastman, D.A., Odom, T.W., and Medintz, I.L. (2021). "Gold Nanoparticle Templating Increases the Catalytic Rate of an Amylase, Maltase, and Glucokinase Multienzyme Cascade through Substrate Channeling Independent of Surface Curvature." ACS Catal. 11(2): 627-638.

Klein, W.P., Thomsen, R.P., Turner, K.B., Walper, S.A., Vranish, J., Kjems, J., Ancona, M.G., and Medintz, I.L. (2019). "Enhanced Catalysis from Multienzyme Cascades Assembled on a DNA Origami Triangle." ACS Nano. 13(12): 13677-13689.

(Continued)

*Primary Examiner* — Ganapathirama Raghu
(74) *Attorney, Agent, or Firm* — US Naval Research Laboratory; Fariborz Moazzam

(57) ABSTRACT

Described herein is a one-pot, four-enzyme cascade of enzymes, three bound to quantum dots with one enzyme free in solution, for the conversion in vitro of fumarate to 1,3-diaminopropane. The cascade operates via two distinctly different enzymatic channeling mechanisms which simultaneously function to increase the overall rate. The first three enzymes of the pathway (AspB->LysC->Asd) were able to engage in channeling in a nanoparticle displayed format, but addition of the last two enzymes to this pathway in this format (AspB->LysC->Asd->Dat->Ddc) did not result in complete channeling through the entire pathway to the final diaminopropane product. Surprisingly, replacement of the last two enzymes (Dat->Ddc) with a naturally occurring fused Dat-Ddc hybrid (Daba) provided for full channeling in this system (AspB->LysC->Asd->Daba).

4 Claims, 14 Drawing Sheets

Specification includes a Sequence Listing.

(56)         References Cited

PUBLICATIONS

Breger, J.C., Oh, E., Susumu, K., Klein, W.P., Walper, S.A., Ancona, M.G., and Medintz, I.L. (2019). "Nanoparticle Size Influences Localized Enzymatic Enhancement—a Case Study with Phosphotriesterase." Bioconjugate Chem. 30 (7): 2060-2074.

Vranish, J.N., Ancona, M.G., Oh, E., Susumu, K., Aragonés, G.L., Breger, J.C., Walper, S.A., and Medintz, I.L. (2018). "Enhancing Coupled Enzymatic Activity by Colocalization on Nanoparticle Surfaces: Kinetic Evidence for Directed Channeling of Intermediates." ACS Nano 12(8): 7911-7926.

Malanoski, A.P., Breger, J.C., Brown, C.W., Deschamps, J.R., Susumu, K., Oh, E., Anderson, G.P., Walper, S.A., and Medintz, I.L. (2017). "Kinetic Enhancement in High-Activity Enzyme Complexes Attached to Nanoparticles." Nanoscale Horiz. 2(5): 235-304.

Vranish, J.N., Ancona, M.G., Oh, E., Susumu, K., and Medintz, I.L. (2017). "Enhancing Coupled Enzymatic Activity by Conjugating One Enzyme to a Nanoparticle." Nanoscale 9(16): 5172-5187.

Susumu, K., E. Oh, J. B. Delehanty, J. B. Blanco-Canosa, B. J. Johnson, V. Jain, W. J. Hervey, W. R. Algar, K. Boeneman, P. E. Dawson and I. L. Medintz (2011). "Multifunctional Compact Zwitterionic Ligands for Preparing Robust Biocompatible Semiconductor Quantum Dots and Gold Nanoparticles." Journal of the American Chemical Society 133(24): 9480-9496.

Dunn, M.F., D. Niks, H. Ngo, T.R.M. Barends, and I. Schlichting (2008). "Tryptophan Synthase: the Workings of a Channeling Nanomachine." Trends in Biochemical Science 33(6): 254-264.

Chae, T.U., Kim, W.J., Choi, S., Park, S.J., and S.Y. Lee (2015). "Metaboloic engineering of Escherichia coli for the production of 1,3-diaminopropane, a three carbon diamine." Scientific Reports 5: 13040.

Lee, J., Sperandio, V., Frantz, D.E., Longgood, J., Camilli, A., Phillips, M.A., and A.J. Michael (2009). An Alternative Polyamine Biosynthetic Pathway Is Widespread in Bacteria and Essential for Biofilm Formation in Vibrio cholerae. The Journal of Biological Chemistry 284(15): 9899-9907.

Breger, J.C., Vranish, J.N., Oh, E., Stewart, M.H., Susumu, K., Lasarte-Aragones, G., Ellis, G.A., Walper, S.A., Diaz, S.A., Hooe, S.L., Klein, W.P., Thakur, M., Ancona, M.G., Medintz, I.L. Self assembling Nanoparticle Enzyme Clusters Provide Access to Substrate Channeling in Multienzymatic Cascades. Nature Communications 14, 1757 (2023).

MULTI-MECHANISTIC CHANNELING WITHIN A BIOCATALYTIC CASCADE FOR THE PRODUCTION OF 1,3-DIAMINOPROPANE

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, DC 20375, USA; +1.202.767.7230; techtran@nrl.navy.mil, referencing NC 211316.3333

CROSS-REFERENCE TO RELATED APPLICATIONS

This application is related to U.S. Pat. No. 11,512,305.

INCORPORATION BY REFERENCE

This Application incorporates by reference the Sequence Listing XML file submitted herewith via the patent office electronic filing system having the file name "sequences-211316US1.xml" and created on May 11, 2023 with a file size of 10,281 bytes.

BACKGROUND

A desire to harness the full potential of synthetic biology continues to drive research interest with corresponding government, academic, and commercial investment. Within the field of synthetic biology, minimalist cell-free biosynthesis represents an appealing avenue of research because it enables the understanding of a single enzymatic pathway while bypassing competing reaction pathways, inhibition, and possible cellular toxicity. Specifically, minimalist cell-free biosynthesis focuses only on the requirements for product formation, meaning just the key enzyme(s), cofactor(s), and substrate. This approach enables the systematic design and optimization of individual biosynthetic pathways prior to assimilation within a more complex matrix and avoids the need for techniques involving living cells, which can undesirably entail competitive, inhibitory, toxic, and/or deleterious pathways.

A need exists for new techniques in synthetic biology.

BRIEF SUMMARY

Described herein is a one-pot, four-enzyme cascade that contains two distinctly different enzyme channeling mechanisms operating simultaneously to increase the rate of fumarate conversion to 1,3-diaminopropane (DAP) in vitro with certain of the enzymes assembled on quantum dots (QDs).

In a first embodiment, an enzymatic cascade includes metallic quantum dots (QDs) with a plurality of enzymes bound thereto, the plurality of enzymes comprising three enzymes comprising SEQ ID NOs: 1, 2, and 3, respectively, and a fourth enzyme having SEQ ID NO: 6 not bound to the QDs but instead free in solution.

In another embodiment, a method of conducting a cascade reaction includes providing an enzymatic cascade according to the first embodiment; contacting the enzymatic cascade with fumarate; and allowing a reaction to proceed so that each of the plurality of enzymes acts in succession to produce 1,3-diaminopropane from the fumarate.

BRIEF DESCRIPTION OF THE DRAWINGS

FIG. 2B depicts a comparison of free (black) and QD-immobilized (red) at 200 nM AspB, 150 nM LysC, and 35 nM Asd for a total enzyme concentration of 385 nM with 300 nM QD. FIG. 2C depicts a comparison of free (black) and QD-immobilized (red) at 180 nM AspB, 135 nM LysC, and 31.5 nM Asd for a total enzyme concentration of 346.5 nM with 135 nM QD. FIG. 2D depicts a comparison of free (black) and QD-immobilized (red) at 160 nM AspB, 120 nM LysC, and 28 nM Asd for a total enzyme concentration of 308 nM with 120 nM QD. All data was obtained in 120 mM HEPES (pH 8) at 30° C. The difference between the on and off QD plots provide strong evidence for channeling taking place because channeling manifests as an increase in the initial rate of kinetic flux versus configurations where the enzymes are freely diffusing in solution and are diffusion limited.

DETAILED DESCRIPTION

Definitions

Figure 1A:
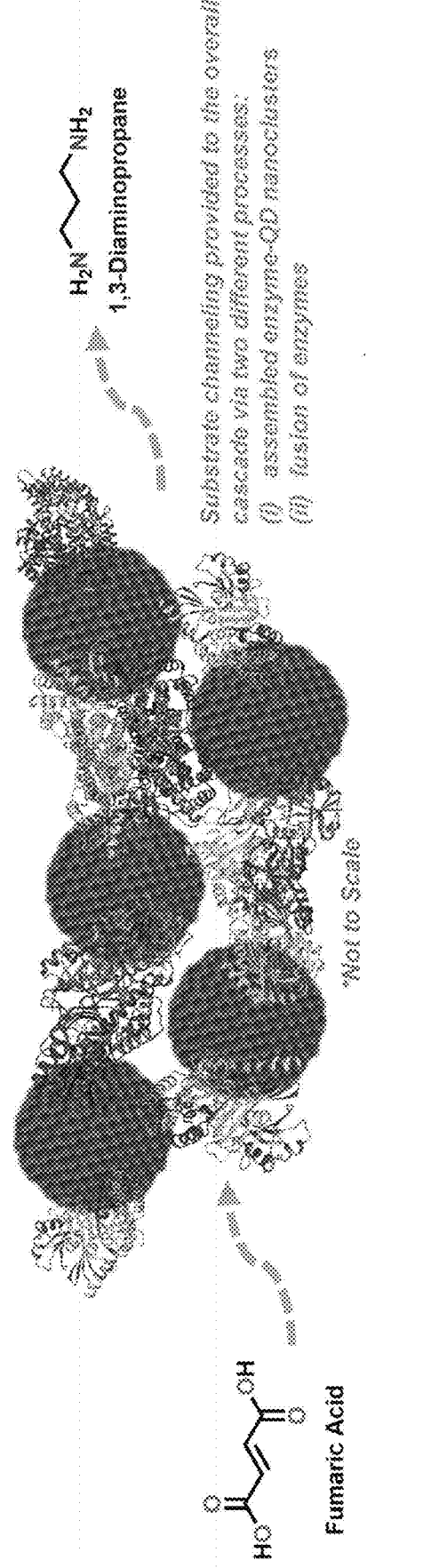
FIG. 1A is a schematic of self-assembled QD-enzyme clusters that make up a multi-enzyme cascade capable of substrate channeling for the conversion of fumaric acid to 1,3-diaminopropane.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

The compound 1,3-diaminopropane is a molecule relevant for the production of plastics and it is also a precursor in the synthetic route to a wide variety of heterocyclic compounds, among other uses. Current industrial methods of 1,3-diaminopropane production require pressures of 10-20 MPa, temperatures of 70-100° C., and a large excess of ammonia. Therefore, developing an alternative green synthetic route to 1,3-diaminopropane that can proceed at room temperature and atmospheric pressure is highly desirable.

In view of previous successes with enhancing enzyme pathways through QD display (described in, for example, U.S. Pat. No. 11,512,305), a technique was sought for a multi-enzyme cascade converting fumaric acid to DAP, a molecule relevant for the synthesis of various heterocycles and the production of polyamide plastics. A five-enzyme cascade (see FIG. 1), using enzymes of varied bacterial origins, was initially established where enzymes were self-assembled stepwise with QDs into nanoclusters and increasing numbers of linked cascade steps were tested for their ability to engage in channeling.

Encouragingly, nanocluster-induced proximity channeling could be maintained in assemblies extending up to the first three steps producing aspartate semialdehyde. However, extending from this by adding the last two enzymes yielded minimal final product. A surprising solution was found in that replacing the Dat and Dbc enzymes with a naturally occurring fusion protein Dat-Ddc hybrid (Daba) rescued the nanoparticle-assembled system provided for full channeling (AspB->LysC->Asd->Daba).

Within the biosynthetic cascade described herein, the first mechanism for channeling is observed when the first three enzymes are immobilized onto the QD surface in close proximity to one another. The first enzyme in the cascade is aspartate ammonia lyase originating from *Bacillus subtilis* (AspB, Enzyme Commission—EC Number 4.3.1.1), which catalyzes the conversion of fumaric acid to aspartic acid. The aspB gene utilized here encodes a 51.6 kDa monomer (SEQ ID NO: 1) which then assembles into the final 206.4 kDa tetramer. The second enzyme in the cascade, aspartokinase III originating from *Escherichia coli* (LysC, EC Number 2.7.2.4) catalyzes the phosphorylation of the aspartic acid product from AspB to form the aspartyl phosphate product utilizing the adenosine triphosphate (ATP) co-factor. The lysC gene utilized here encodes a 48.5 kDa structure (SEQ ID NO: 2) which then assembles into the final 97 kDa homodimer. The third enzyme in the cascade, aspartate-β-semialdehyde dehydrogenase originating from *E. coli* (Asd, EC Number 1.2.1.11), catalyzes the conversion of aspartyl phosphate product from LysC to the aspartate semialdehyde product employing the nicotinamide adenine dinucleotide phosphate (NADPH) co-factor. The asd gene utilized here encodes a 40 kDa structure (SEQ ID NO: 3) which then assembles into the final 80kDa homodimer. The AspB, LysC, and Asd enzymes make up what is defined as the first three-enzyme cascade for the conversion of fumaric acid to aspartate semialdehyde.

The second mechanism for channeling is observed within a fusion enzyme that converts the aspartate semialdehyde from the three-enzyme cascade to 1,3-diaminopropane. The fusion enzyme originating from *Vibrio cholerae* (Daba, SEQ ID NO: 6), functions as a fused dual enzyme system for the conversion of aspartate semialdehyde to 1,3-diaminopropane. The channeling mechanism with the fusion enzyme does not arise from proximity or probabilistic channeling when immobilized onto the QD surface. Instead, for the fusion enzyme, the second observed channeling mechanism arises from intramolecular substrate activation and transfer within the fused dual enzyme system. The AspB, LysC, Asd, and Daba enzymes make up the four-enzyme cascade for the conversion of fumaric acid to 1,3-diaminopropane where the first three enzymes are assembled to QDs.

The fused dual enzyme of Daba were compared against the two enzymes individually, as a non-fused system for comparison. The enzyme 2-ketoglutarate 4-aminotransferase (Dat, EC Number 2.6.1.76) originating from *Acinetobacter baumannii* but herein recombinantly produced in *E. coli* catalyzes the conversion of the aspartate semialdehyde product from Asd to diaminobutyric acid product in the presence of glutamic acid. The dat gene utilized here encodes a 48.8 kDa structure (SEQ ID NO: 4) which then assembles into the final 195.2 kDa tetrameric structure. The second enzyme from the fused enzyme in the cascade, L-2,4-diaminobutyrate decarboxylase originating from A. baumannii (Ddc, EC Number 4.1.1.86), converts the diaminobutyric acid product from Dat to the final DAP product via concomitant release of carbon dioxide. The Ddc gene utilized here encodes a 56.3 kDa structure (SEQ ID NO: 4). The AspB, LysC, Asd, Dat, and Ddc enzymes make up what is termed the five-enzyme cascade for the conversion of fumaric acid to DAP.

Figure 1B:
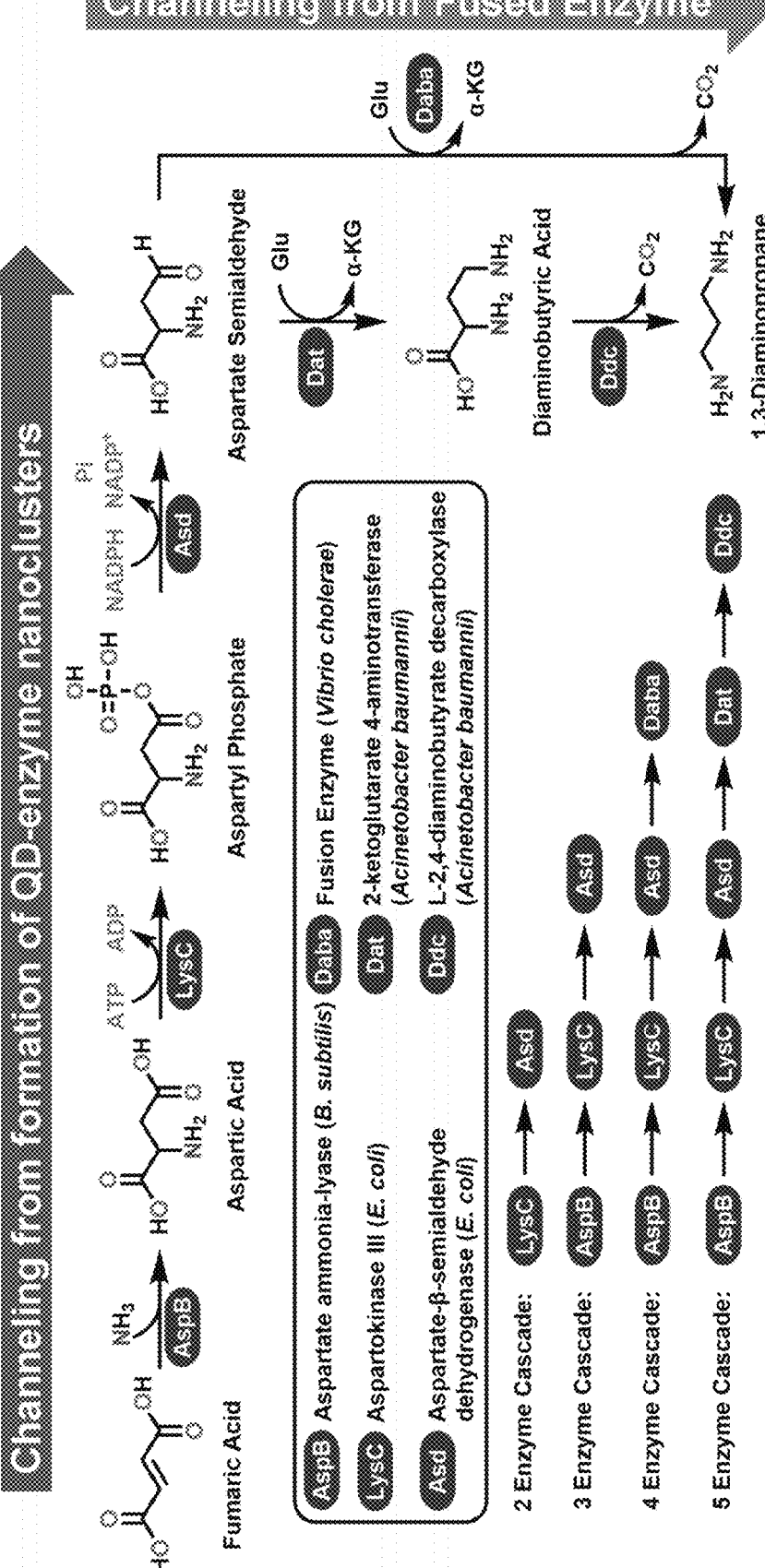
FIG. 1B depicts the multi-enzyme cascade of focus in this study. Glu=L-glutamic acid, α-KG=alpha-Ketoglutaric acid, ATP=adenosine triphosphate, ADP=adenosine diphosphate, NADPH=nicotinamide adenine dinucleotide phosphate hydrogen, NADP+=nicotinamide adenine dinucleotide phosphate, Pi=inorganic phosphate.

FIG. 1A displays a schematic for the conversion of fumaric acid to DAP via a self-assembled enzyme-QD aggregate where multiple enzymes are bound to one or more QDs which are then cross-linked together into small nano-clusters via diffusion limited aggregation. The enzyme-QD aggregate formation utilized here is based on metal affinity coordination between terminal hexahistidines displayed on the enzymes which bind to the ZnS shell of the QDs by a high affinity interaction. This represents a well-established self-assembly process. The number of QDs that a single enzyme will bind is dependent on the structure of the enzyme (monomer, dimer, trimer, tetramer, etc.), where for example, an enzyme that exists as a dimer would be expected to be able to bind to up to two QDs depending, of course, on where the QD binding site is on the enzyme. The enzyme-QD aggregate puts enzymes in close proximity to one another and represents one of the two avenues of channeling in this work, namely through either proximity of active sites in a fusion or by forming enzyme-QD clusters. The second avenue of channeling arises from the fusion enzyme, Daba, which also engages in channeling of the diaminobutyric acid intermediate which arises from the fused (i.e., closely linked) Dat-Ddc system. FIG. 1B depicts a structural scheme for the substrates, intermediates, products, and enzymes in the pathway and the conversion reaction each enzyme is responsible for.

Figure 2A:
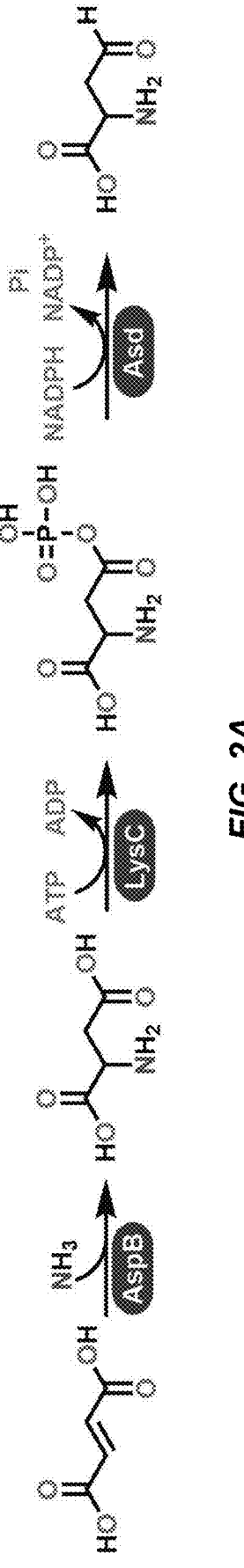
FIG. 2A provides a schematic of the three-enzyme pathway for the conversion of fumaric acid to aspartate semialdehyde.
Figure 2C:
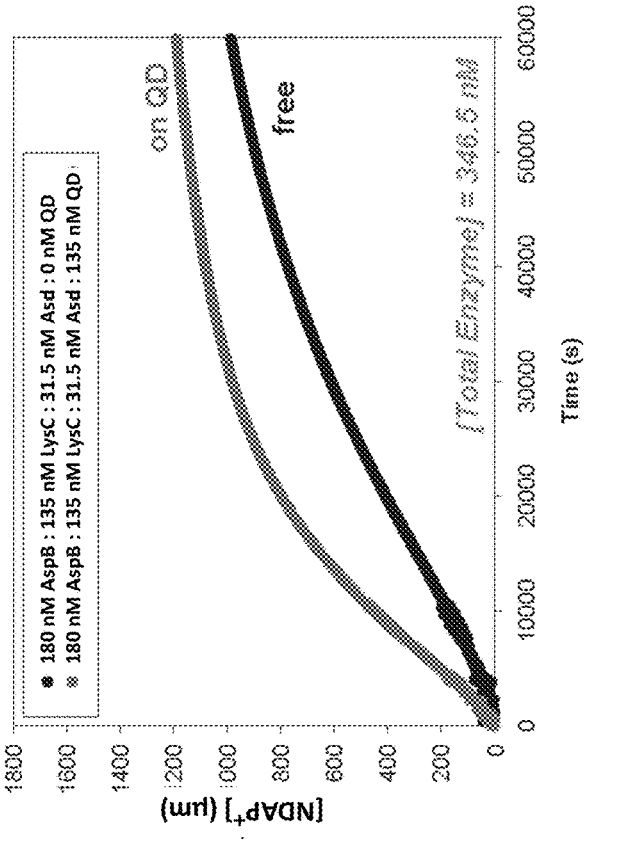
FIGS. 2B-2D show results from a dilution assay monitoring the formation of $NADP^+$ over time to support the effect of channeling in the three-enzyme pathway involving AspB, LysC, and Asd with 1.5 mM NADPH, 15 mM ATP, 17.5 mM $MgCl_2 \cdot 6H_2O$, 12.5 mM fumaric acid, and 200 mM $NH_4Cl$.
Figure 2B:
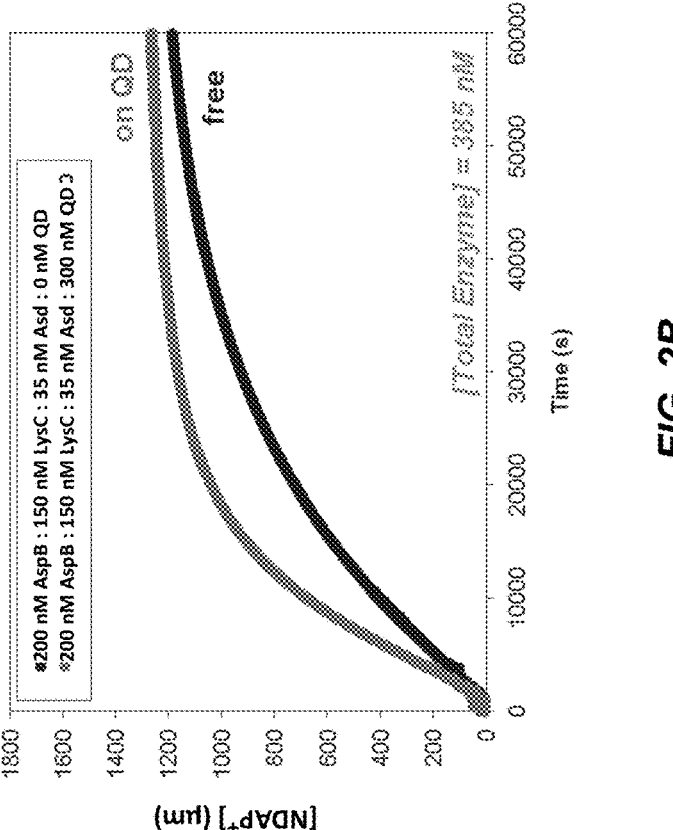
Figure 2D:
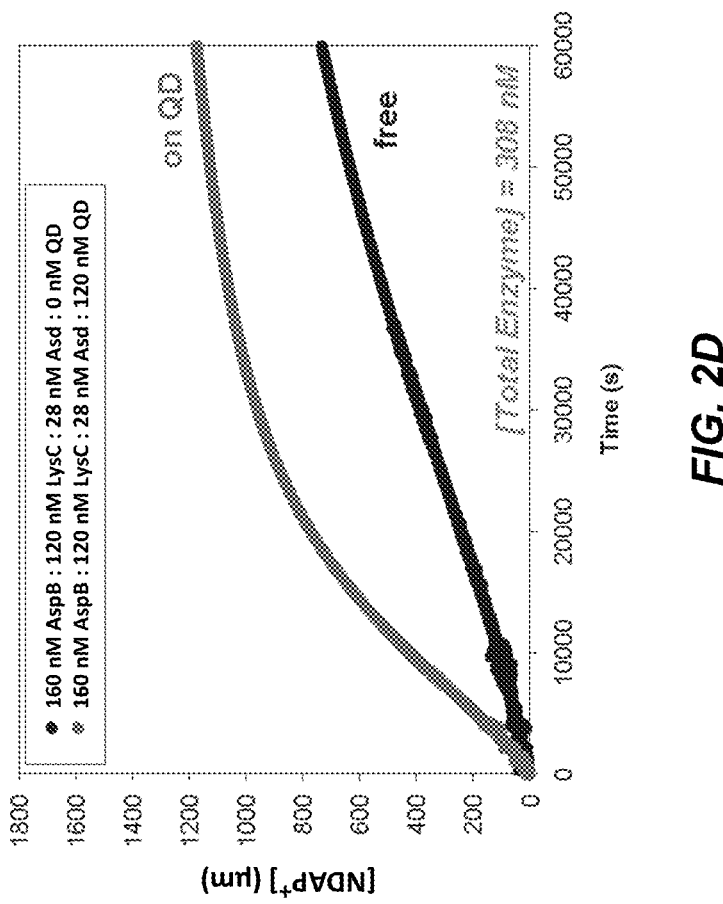

FIG. 2A shows is a schematic of the three-enzyme cascade involving AspB, LysC and Asd for the conversion of fumaric acid to aspartate semi-aldehyde. FIGS. 2B-2D provide representative data to support the channeling mechanism via QD immobilization in this work. The plots in FIGS. 2B-2D are plots of the concentration of $NADP^+$ versus time. $NADP^+$ is the co-factor byproduct involved in the final step of the three-enzyme cascade (FIG. 2A). Therefore, by monitoring the formation of $NADP^+$ via the consumption of NADPH at 340 nm in the UV-vis, the overall progress of this reaction can be monitored. For the data shown in FIGS. 2B-2D, the black traces are obtained when all three enzymes are freely diffusing in solution and the red traces are when the enzymes are immobilized onto the QD surface. Enzyme immobilization was carried out via an established self-assembly process, where all three of the enzymes were mixed together and then subsequent addition of QD initiated the enzyme assembly process through the $His_6$ tag on the end terminus of each enzyme. As the total concentration of enzyme decreases from 385 nM (FIG. 2B) to 346.5 nM (FIG. 2C) and finally to 308 nM (FIG. 2D) the difference in activity between the freely diffusing enzymes (FIGS. 2B-2D, black) and those that are QD immobilized (FIGS. 2B-2D, red) subsequently increases. Notably, this trend holds for the initial rate region (the initial linear portion of the plots in FIGS. 2B-2D, prior to the plateau region) of the reaction which is indicative of the presence of a channeling mechanism. The enzyme concentrations for the data shown in FIGS. 2B-2D were selected based on the catalytic rates of the individual enzymes which were identified and optimized in preliminary work for this study and the concentration of QD was selected based off of a QD titration study where the ratio of QD to enzyme was also optimized. This same strategy was applied to developing assays throughout all work described herein. These results confirm that when AspB, LysC, and Asd are co-immobilized onto the QD surface, the three enzymes are capable of channeling substrates and intermediates between each other in order to minimize diffusion into the bulk solution which is what occurs when the three enzymes are freely diffusing in solution. Competing diffusion of substrates and/or intermediates into the bulk solution functions to lower reaction rates and efficiency, therefore by immobilizing the enzymes in close proximity to one another on the QD surface, as we have shown for the three-enzyme cascade, the effects of bulk diffusion are minimized and the rates and efficiency of the reaction are increased. Overall, the data in FIGS. 2B-2D represents one of the two mechanisms for channeling in the multi-enzyme cascade for the conversion of fumaric acid to 1,3-diaminopropane.

Figure 3A:
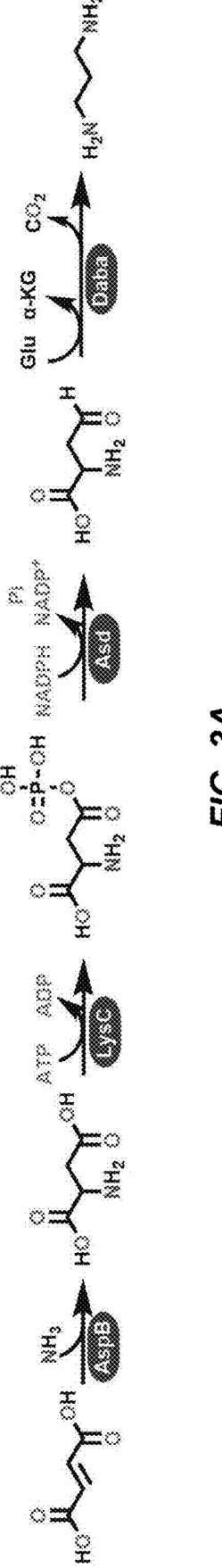
FIG. 3A shows a schematic of the four-enzyme pathway for the conversion of fumaric acid to 1,3-diaminopropane with the Daba enzyme.
Figure 3C:
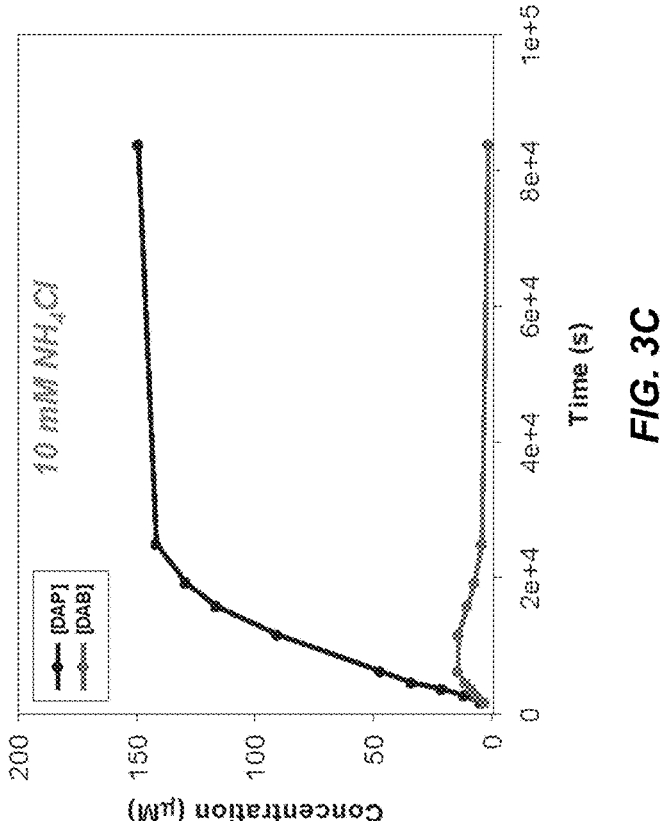
FIGS. 3B-3D provide comparisons of diaminobutyric acid formation/consumption (red) and 1,3-diaminopropane formation (black) for the four-enzyme cascade across increasing $NH_4Cl$ concentrations. Conditions: 180 nM AspB, 80 nM LysC, 24 nM Asd, 50 nM QD, 30 nM Daba, 0.5 mM pyridoxal-5-phosphate, 20 mM glutamate, 5 mM NADPH, 15 mM ATP, 17.5 mM $MgCl_2 \cdot 6H_2O$, and 0.5 mM fumaric acid. For QD-enzyme assembly 180 nM AspB, 80 nM LysC, and 24 nM Asd assembled onto 50 nM QD. Then 2500 nM blocking peptide used before adding in the 30 nM Daba. All data was obtained in 120 mM HEPES (pH 8) at room temperature.
Figure 3B:
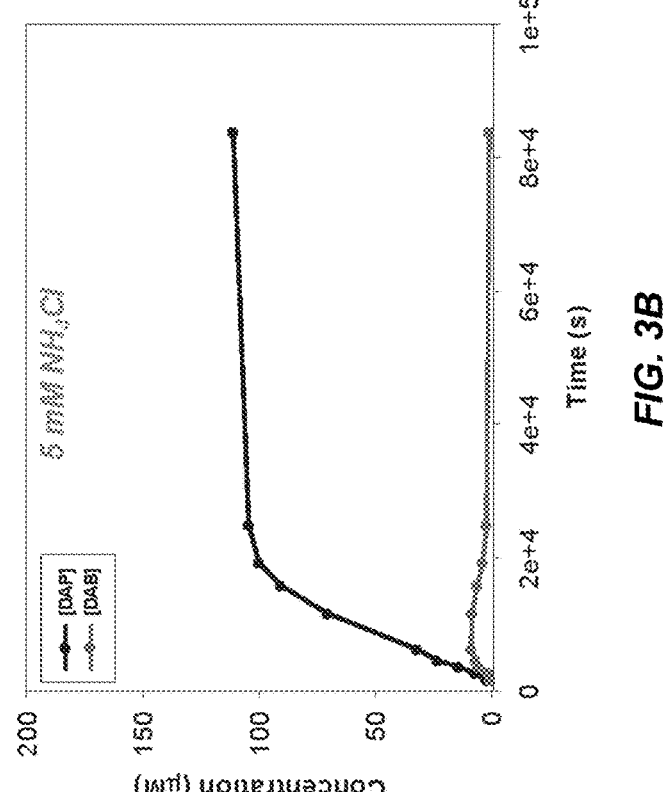
Figure 3E:
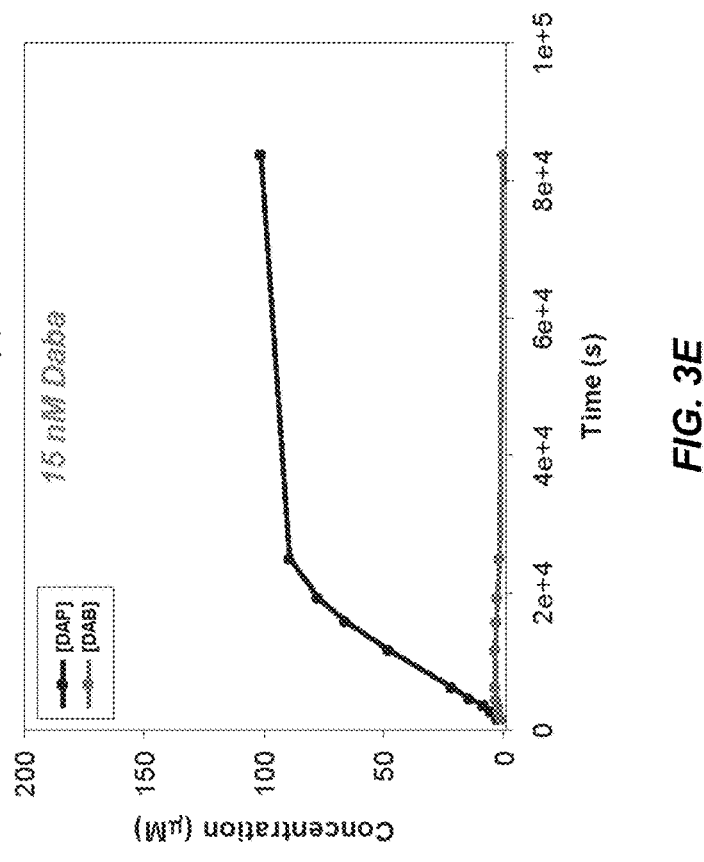
FIGS. 3E-3G provide comparisons of diaminobutyric acid formation/consumption (red) and 1,3-diaminopropane formation (black) for the four-enzyme cascade across increasing Daba concentrations. Conditions: 180 nM AspB, 80 nM LysC, 24 nM Asd, 50 nM QD, 0.5 mM pyridoxal-5-phosphate, 20 mM glutamate, 5 mM NADPH, 15 mM ATP, 17.5 mM $MgCl_2x6H2O$, 100 mM $NH_4Cl$ and 0.5 mM fumaric acid. For QD-enzyme assembly 180 nM AspB, 80 nM LysC, and 24 nM Asd assembled onto 50 nM QD. Then 2500 nM blocking peptide used before adding in the Daba enzyme. All data was obtained in 120 mM HEPES (pH 8) at room temperature. The three-enzyme cascade was QD immobilized by adding QD to a mixture containing AspB, LysC, and Asd and allowing assembly to take place. Then peptide blocker was added to the mixture at the indicated concentration. The peptide blocker functions to block any open remaining Hiss coordination sites so that lastly the Daba enzyme can be added into the mixture and remain a freely diffusing enzyme in solution.
Figure 3D:
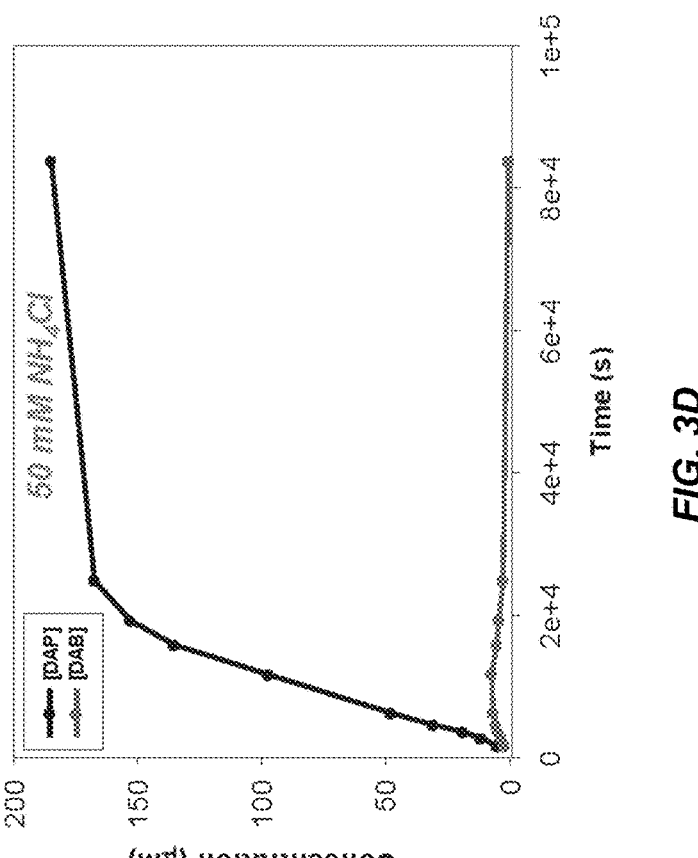
Figure 3G:
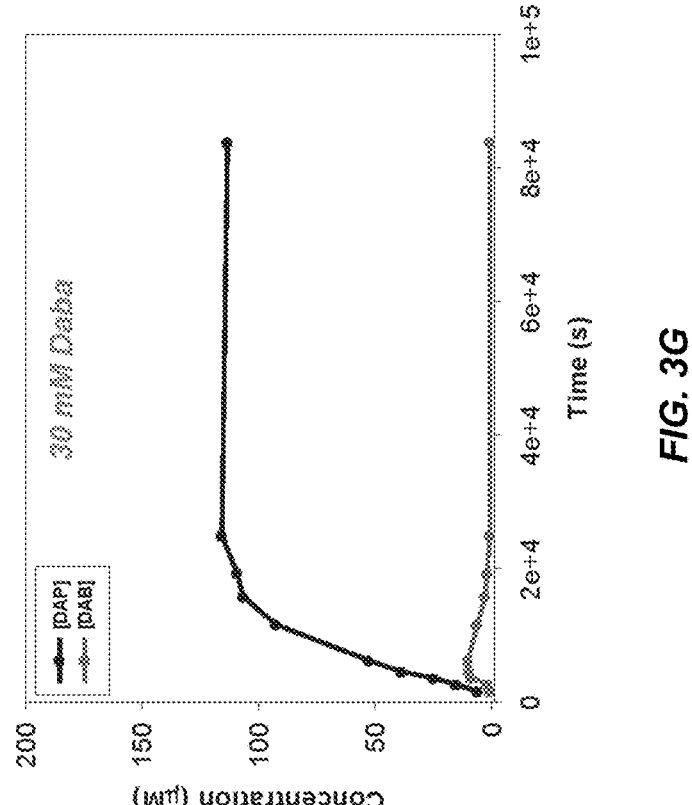
Figure 3F:
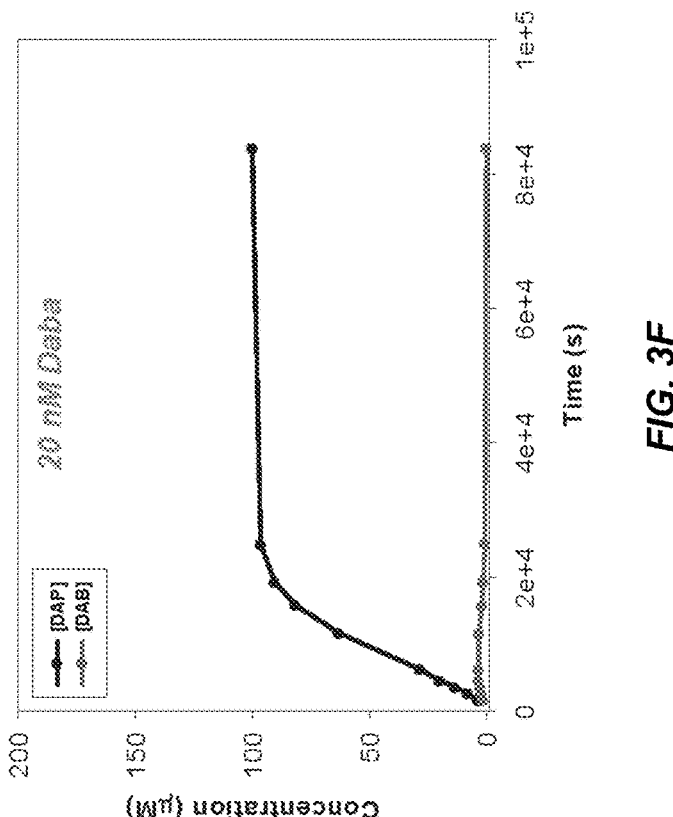

FIG. 3A shows a schematic of the four-enzyme cascade involving AspB, LysC, Asd, and Daba for the conversion of fumaric acid to 1,3-diaminopropane. The plots in FIGS. 3B-3G are plots of either the concentration of the diaminobutyric acid intermediate (red) or the 1,3-diaminopropane product (black) versus time for the four-enzyme cascade where the first three enzymes of the cascade, AspB, LysC and Asd, are immobilized onto the QD surface and the Daba enzyme is freely diffusing in solution. This was accomplished by performing the self-assembly process with the three-enzyme cascade, as described above, and then introducing a peptide blocker into the AspB/LysC/Asd/QD mixture. The peptide blocker functions to block any open remaining Hiss coordination sites so that lastly the Daba enzyme can be added into the mixture and remain a freely diffusing enzyme in solution. These reactions were run in vials and aliquots of the reaction mixture were removed at recorded time points and the amount of diaminobutyric acid and 1,3-diaminopropane was quantified via LCMS. The data in FIGS. 3B-3D spans across variable $NH_4Cl$ concentrations while the concentration of fumaric acid, enzyme, QD, and any other substrates/co-factors remain unchanged. The data in FIGS. 3E-3G spans across variable Daba concentrations while the concentration of all substrates/co-factors, QD, AspB, LysC, and Asd remain unchanged. From these data, it is clear that across all variable $NH_4Cl$ (FIGS. 3B-3D) and variable Daba (FIGS. 3E-3G) data, conversion of fumaric acid to 1,3-diaminopropane is occurring for the four enzyme cascade. Notably, all control reactions in the absence of the enzyme do not produce 1,3-diaminopropane. Additionally, monitoring the amount of the intermediate diaminobutyric acid demonstrates that during the course of the reaction, the rate of diaminobutyric acid formation is nearly identical to the rate of diaminobutyric acid consumption. This means that nearly all the diaminobutyric acid is being consumed as it is produced showing that there is not a significant buildup of the diaminobutyric acid intermediate relative to the amount of 1,3-diaminopropane product being produced.

Figure 4A:
FIG. 4A depicts a schematic of the five-enzyme pathway for the conversion of fumaric acid to 1,3-diaminopropane.
Figure 4C:
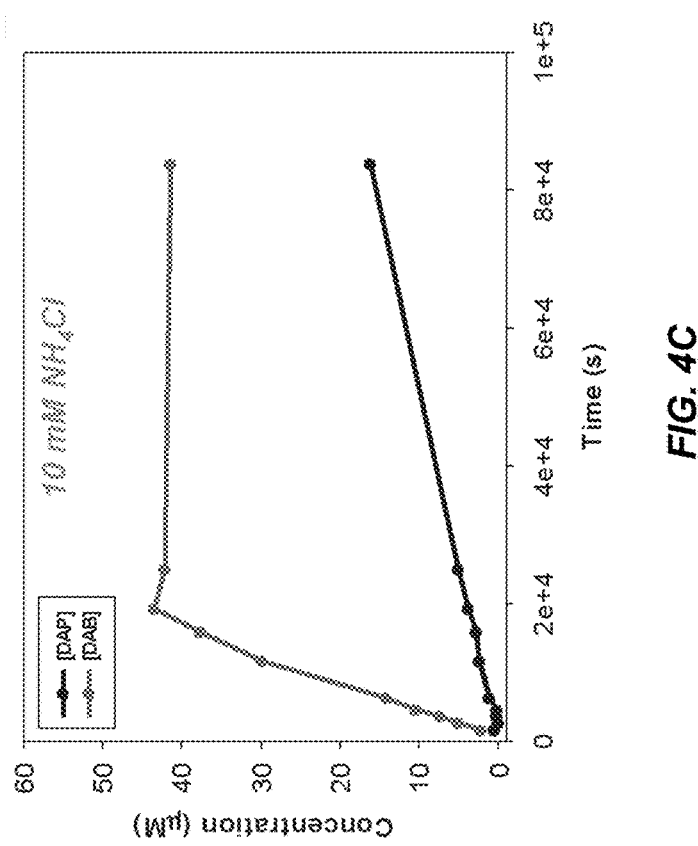
FIGS. 4B-4D show comparisons of diaminobutyric acid formation/consumption (red) and 1,3-diaminopropane formation (black) for the four-enzyme cascade across increasing NH$_4$Cl concentrations. Conditions: 180 nM AspB, 80 nM LysC, 24 nM Asd, 50 nM QD, 10 nM Dat, 10 nM Ddc, 0.5 mM pyridoxal-5-phosphate, 20 mM glutamate, 5 mM NADPH, 15 mM ATP, 17.5 mM MgCl$_2$·6H$_2$O, and 0.5 mM fumaric acid. For QD-enzyme assembly 180 nM AspB, 80 nM LysC, and 24 nM Asd assembled onto 50 nM QD. Then 2500 nM blocking peptide used before adding in 10 nM Dat and 10 nM Ddc. All data was obtained in 120 mM HEPES (pH 8) at room temperature.
Figure 4B:
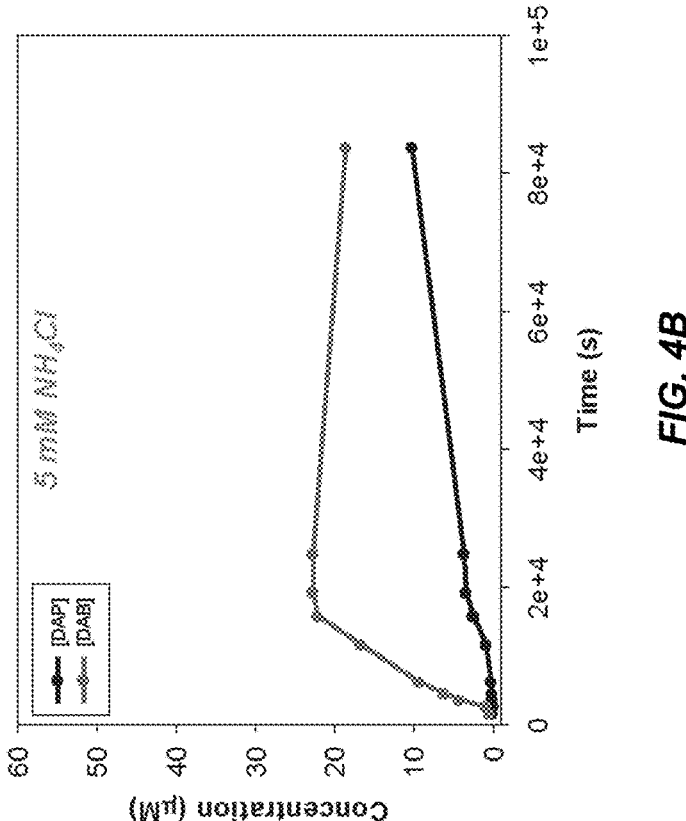
Figure 4E:
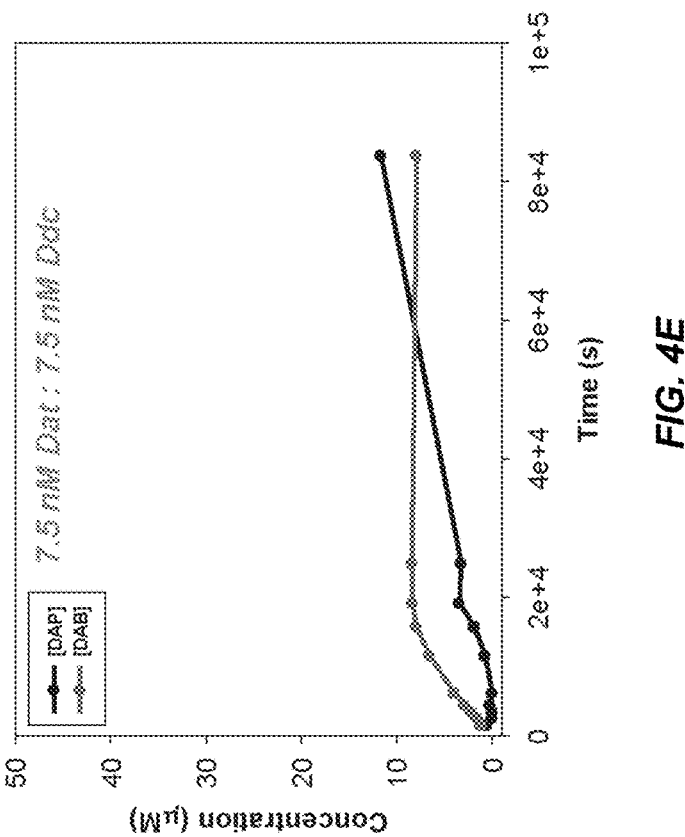
FIGS. 4E-4G provide comparisons of diaminobutyric acid formation/consumption (red) and 1,3-diaminopropane formation (black) for the four-enzyme cascade across increasing Dat and Ddc concentrations. Conditions: 180 nM AspB, 80 nM LysC, 24 nM Asd, 50 nM QD, 0.5 mM pyridoxal-5-phosphate, 20 mM glutamate, 5 mM NADPH, 15 mM ATP, 17.5 mM MgCl$_2$·6H$_2$O, 100 mM NH$_4$Cl and 0.5 mM fumaric acid. For QD-enzyme assembly 180 nM AspB, 80 nM LysC, and 24 nM Asd assembled onto 50 nM QD. Then 2500 nM blocking peptide used before adding in the Dat and Ddc enzymes. All data was obtained in 120 mM HEPES (pH 8) at room temperature. The three-enzyme cascade was QD immobilized by adding QD to a mixture containing AspB, LysC, and Asd and allowing assembly to take place. Then peptide blocker was added to the mixture at the indicated concentration. The peptide blocker functions to block any open remaining Hiss coordination sites so that lastly the Dat and Ddc enzymes can be added into the mixture and remain a freely diffusing enzyme in solution.
Figure 4D:
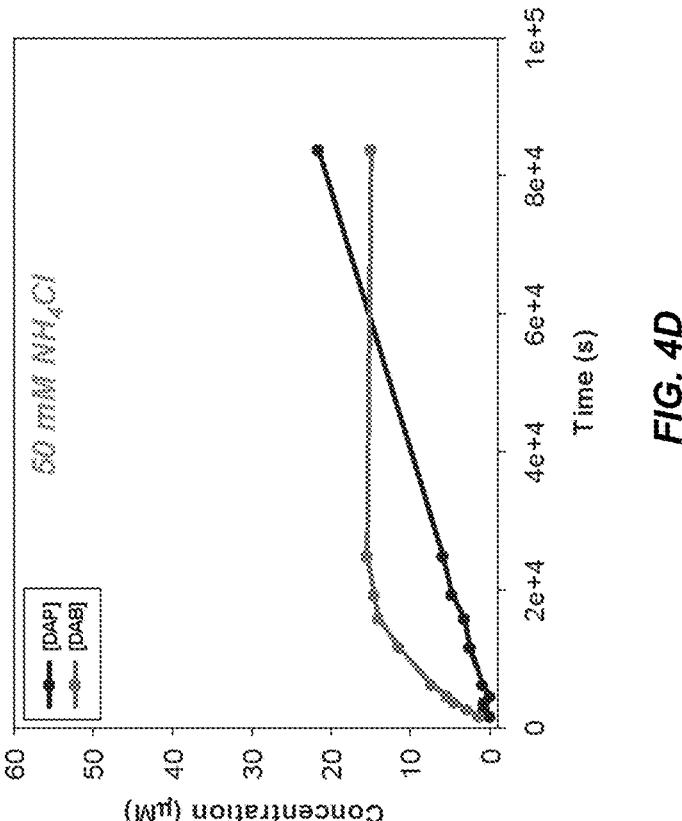
Figure 4G:
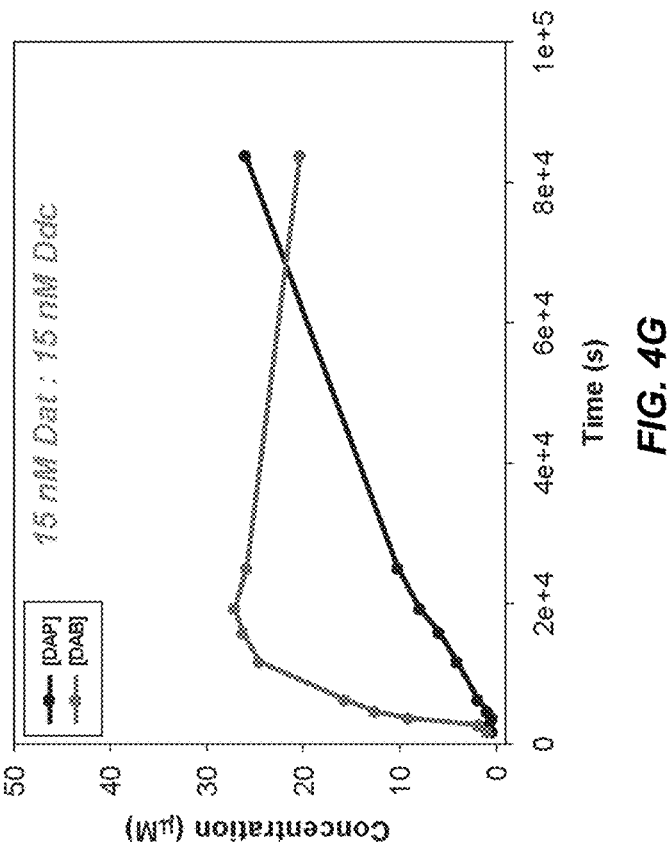
Figure 4F:
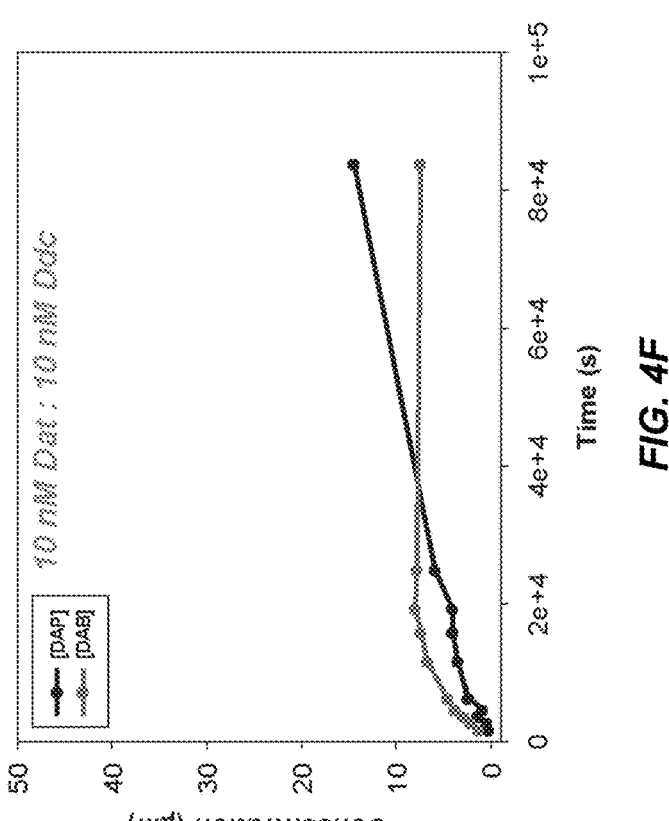

FIG. 4A is a schematic of the five-enzyme pathway involving AspB, LysC, Asd, Dat, and Ddc for the conversion of fumaric acid to 1,3-diaminopropane. The data in FIGS. 4B-G was obtained under identical conditions to the data in FIGS. 3B-3G, with the only difference being that for FIGS. 4B-G, the individual Dat and Ddc enzymes were used as an alternative to the Daba enzyme. Dat and Ddc represent the non-fused form of Daba. The plots in FIGS. 4B-G are plots of either the concentration of the diaminobutyric acid intermediate (red) or the 1,3-diaminopropane product (black) versus time for the five-enzyme cascade where the first three enzymes of the cascade, AspB, LysC and Asd, are immobilized onto the QD surface and the Dat and Ddc enzymes are freely diffusing in solution. This was accomplished utilizing the peptide blocker in an analogous manner as described above for the four-enzyme cascade. The data was obtained as a way to compare the activity of the four-enzyme cascade to that of the five-enzyme cascade. As can be seen across variable $NH_4Cl$ concentrations (FIGS. 4B-D) and variable Dat/Ddc concentrations (FIGS. 4E-G), there are two distinguishing features that persist when this data is compared to the four-enzyme cascade (FIGS. 3B-3G). One, is that the overall amount of 1,3-diaminopropane produced in the five-enzyme cascade (FIGS. 4B-G) is significantly lower than what is produced by the four-enzyme cascade within the time window (i.e., the rate of formation of DAP is significantly lower in the five-enzyme cascade than the four-enzyme cascade). Second, is that for the five-enzyme cascade the rate of intermediate diaminobutyric acid formation and consumption is significantly slower relative to the rate of 1,3-diaminoproane product formation when compared to what was observed for the four-enzyme cascade. Further, when comparing the data in FIGS. 3B-3G to the data in FIGS. 4B-G, it is clear that the five-enzyme cascade requires a much larger buildup of diaminobutyric acid formation to initiate accumulation of the 1,3-diaminopropane product.

Overall, these data demonstrate how using the fusion enzyme, Daba, enables a more efficient conversion of the diaminobutyric acid intermediate to the 1,3-diaminopropane product, increasing the total yield for the conversion of fumaric acid to 1,3-diaminopropane. The comparison between the four- and five-enzyme cascades identifies the second channeling mechanism present in the multi-enzyme cascade for the conversion of fumaric acid to 1,3-diaminopropane, which is intramolecular substrate channeling within the fusion enzyme, Daba.

Figure 5:
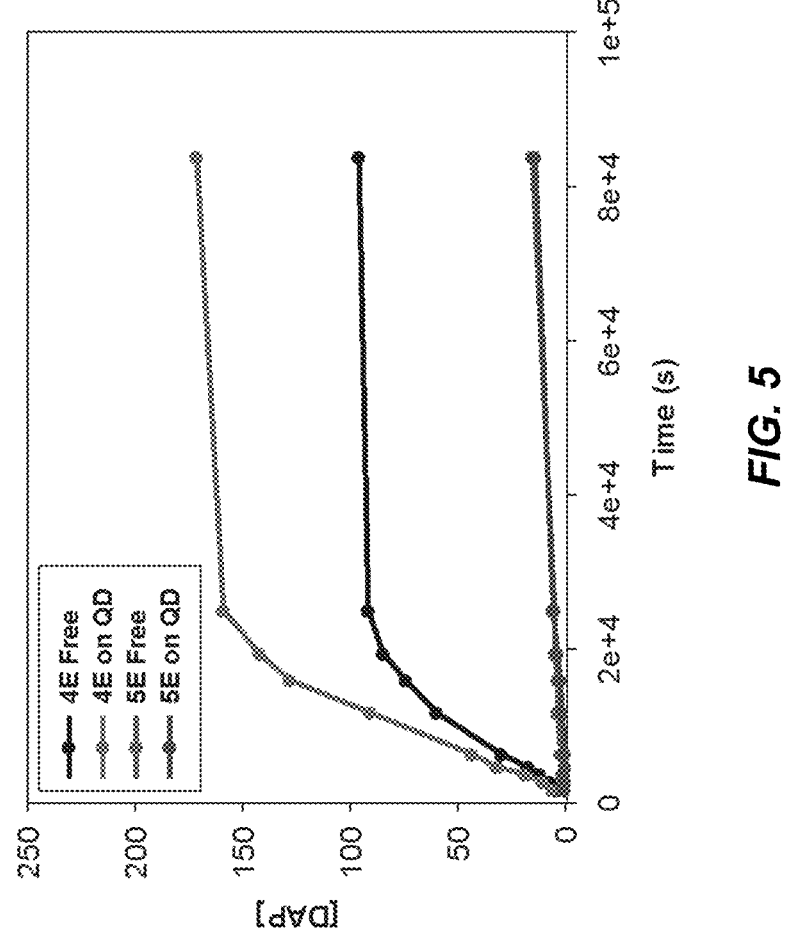
FIG. 5 provides a comparison of the four-enzyme cascade with 50 nM QD (red) and in the absence of QD (black) and comparison of the five-enzyme cascade with 50 nM QD (blue) and in the absence of QD (green). Note that the blue and green traces overlap. Conditions: 180 nM AspB, 80 nM LysC, 24 nM Asd, 50 nM QD, 10 nM Dat when present, 10 nM Ddc when present, 20 nM Daba when present, 0.5 mM pyridoxal-5-phosphate, 20 mM glutamate, 5 mM NADPH, 15 mM ATP, 17.5 mM MgCl$_2$·6H$_2$O, 100 mM NH$_4$Cl, and 0.5 mM fumaric acid. For QD-enzyme assembly 180 nM AspB, 80 nM LysC, and 24 nM Asd assembled onto 50 nM QD. Then 2500 nM blocking peptide used before adding in either 10 nM Dat and 10 nM Ddc or 20 nM Daba. All data was obtained in 120 mM HEPES (pH 8) at room temperature. For the on QD traces, the three-enzyme cascade was QD immobilized by adding QD to a mixture containing AspB, LysC, and Asd and allowing assembly to take place. Then peptide blocker was added to the mixture at the indicated concentration. The peptide blocker functions to block any open remaining Hiss coordination sites so that lastly either the Dat and Ddc enzymes or the Daba enzyme can be added into the mixture and remain a freely diffusing enzyme in solution.

The data in FIG. 5 compares the amount of 1,3-diaminopropane produced for the four- and five-enzyme cascades when AspB, LysC, and Asd are either freely diffusing in solution (FIG. 5, black for the four-enzyme cascade and green for the five-enzyme cascade) or immobilized onto the QD surface (FIG. 5, red for the four-enzyme cascade and blue for the five-enzyme cascade). For the four-enzyme cascade, when the three-enzyme portion of the cascade, which we have shown undergoes proximity channeling when immobilized onto the QD surface, is immobilized on the QD surface with the fusion enzyme, Daba, as freely diffusing, an increase in both the initial rate and overall amount of 1,3-diaminopropane formation is observed (FIG. 5, black versus red). Specifically, comparing the activity of the four-enzyme cascade in the presence and absence of QD results in an increase in the initial rate of 1,3-diaminopropane formation from 0.005 µM/s in the absence of QD immobilization to 0.0086 µM/s when AspB, LysC, and Asd are QD immobilized. Additionally, after 23 hours the freely diffusing four-enzyme cascade reached a final 1,3-diaminopropane concentration of 95.9 µM, while the four-enzyme cascade with AspB, LysC, and Asd QD immobilized reached a 1,3-diaminopropane concentration of 171.2 µM over the same time period. In both the presence and absence of QD immobilization, the amount of 1,3-diaminopropane produced via the four-enzyme cascade vastly surpasses the amount of 1,3-diaminopropane that can be produced by the five-enzyme cascade under otherwise analogous conditions (FIG. 5, green and blue). For the five-enzyme cascade, under comparable conditions both in the presence and absence of QD immobilization, the initial rate of 1,3-diaminopropane formation does not exceed 0.0002 µM/s and did not exceed a 1,3-diaminopropane concentration of 15 µM after 23 hours. These results demonstrate that the dual channeling system identified with the four-enzyme cascade (FIG. 5, red) reaches an initial rate that is 43 times greater than that observed with the five-enzyme cascade (FIG. 5, blue) resulting in an over 10 times greater amount of 1,3-diaminopropane production. Overall, the conversion efficiency for the four enzyme system reaches ~85% while that of the five enzyme system is consistently below 5%

These results were only achieved by combining two distinct mechanisms for channeling, one via QD immobilization and the other via the fusion enzyme. Notably, immobilizing Dat and Ddc onto the QD surface did not result in increasing the production of 1,3-diaminopropane relative to the freely diffusing enzymes. This would suggest that QD immobilization do not bring the Dat and Ddc enzymes in close enough proximity to one another to engage in channeling, which would indicate that there may exist optimal distances and/or modes to channeling that are specific to the individual enzymes engaging in the channeling mechanism. Here, two channeling mechanisms within a single cascade operate simultaneously function to contribute to an increase in product formation. On the whole, these results demonstrate that it is possible to tune the channeling mechanism to a given enzyme and/or reaction step that is most suitable for accessing substrate channeling and that more than one channeling mechanism can be successfully applied to a multi-enzyme cascade to increase product formation.

Further Embodiments

In order to study the channeling phenomenon, the four- and/or five-enzyme cascade reaction can be conducted in the presence of a competitive L-2,4-diaminobutyric acid acetyl-transferase (EctA) enzyme which acetylates one of the DAB amines with Acetyl-CoA towards production of ectoine (see Scheme S6in Appendix 2), the enzyme having SEQ ID NO: 7. Details are provided in the Appendices.

Advantages

The Daba fused enzyme acted to rescue the channeling effect that was disrupted upon addition of the equivalent free enzymes. This effect was surprising and unexpected. Also surprising and unexpected was that the Daba enzyme operated more efficiently when free in solution as compared to being bound to the QDs as with the other enzymes (see Appendix FIG. 3G and Table 1).

This technique provides a number of abilities: to access multiple mechanisms of substrate channeling within a single-pot multienzymatic cascade; to increase the yield of a biocatalytic reaction via multiple mechanisms of substrate channeling in a multienzyme pathway; to increase the efficiency of a biocatalytic reaction via multiple mechanisms of substrate channeling in a multienzyme pathway; to increase the rate of overall kinetic flux via multiple mechanisms of substrate channeling in a multienzyme pathway; to tune the channeling mechanism to a given enzyme and/or reaction step that is most suitable for accessing substrate channeling; and for one type of channeling mechanism to complement and extend channeling in a multienzyme system where another type of channeling is present.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Kummer, M. J., Lee, Y.S., Yuam, M., Alkotaini, B., Zhai, J., Blumenthal E., and Minteer, S. D. (2021). "Substrate Channeling by a Rationally Designed Fusion Protein in a Biocatalytic Cascade." *JACS Au* 1(8): 1187-1197
2. Hooe, S., Breger, J., Dean, S., Susumu, K., Oh, E., Walper, S., Ellis, G. A., and Medintz, I. L. (2022). "Benzaldehyde Lyase Kinetic Improvements, Potential Channeling to Alcohol Dehydrogenase, and Substrate Scope when Immobilized on Semiconductor Quantum Dots." *ACS Appl. Nano Mater.* 5(8): 10900-10911
3. Díaz, S. A., Choo, P., Oh, E., Susumu, K., Klein, W. P., Walper, S. A., Hastman, D. A., Odom, T. W., and Medintz, I.L. (2021). "Gold Nanoparticle Templating Increases the Catalytic Rate of an Amylase, Maltase, and Glucokinase Multienzyme Cascade through Substrate Channeling Independent of Surface Curvature." *ACS Catal.* 11(2):627-638
4. Klein, W. P., Thomsen, R. P., Turner, K. B., Walper, S. A., Vranish, J., Kjems, J., Ancona, M. G., and Medintz, I. L. (2019). "Enhanced Catalysis from Multienzyme Cascades Assembled on a DNA Origami Triangle." *ACS Nano.* 13(12): 13677-13689
5. Breger, J. C., Oh, E., Susumu, K., Klein, W. P., Walper, S. A., Ancona, M. G., and Medintz, I. L. (2019). "Nanoparticle Size Influences Localized Enzymatic Enhancement—A Case Study with Phosphotriesterase." *Bioconjugate Chem.* 30(7): 2060-2074
6. Vranish, J. N., Ancona, M. G., Oh, E., Susumu, K., Aragonés, G.L., Breger, J. C., Walper, S. A., and Medintz, I. L. (2018). "Enhancing Coupled Enzymatic Activity by Colocalization on Nanoparticle Surfaces: Kinetic Evidence for Directed Channeling of Intermediates." *ACS Nano* 12(8):7911-7926
7. Malanoski, A. P., Breger, J. C., Brown, C. W., Deschamps, J. R., Susumu, K., Oh, E., Anderson, G. P., Walper, S. A., and Medintz, I. L. (2017). "Kinetic Enhancement in High-Activity Enzyme Complexes Attached to Nanoparticles." *Nanoscale Horiz.* 2(5): 235-304
8. Vranish, J. N., Ancona, M.G., Oh, E., Susumu, K., and Medintz, I. L. (2017). "Enhancing Coupled Enzymatic Activity by Conjugating One Enzyme to a Nanoparticle." *Nanoscale* 9(16):5172-5187
9. Susumu, K., E. Oh, J. B. Delehanty, J. B. Blanco-Canosa, B. J. Johnson, V. Jain, W. J. Hervey, W. R. Algar, K. Boeneman, P. E. Dawson and I. L. Medintz (2011). "Multifunctional Compact Zwitterionic Ligands for Preparing Robust Biocompatible Semiconductor Quantum Dots and Gold Nanoparticles." *Journal of the American Chemical Society* 133(24):9480-9496.
10. Dunn, M. F., D. Niks, H. Ngo, T. R. M. Barends, and I. Schlichting (2008). "Tryptophan Synthase: The Workings of a Channeling Nanomachine." *Trends in Biochemical Science* 33(6):254-264.
11. Chae, T. U., Kim, W. J., Choi, S., Park, S. J., and S. Y. Lee (2015). "Metaboloic engineering of *Escherichia coli* for the production of 1,3-diaminopropane, a three carbon diamine." *Scientific Reports* 5: 13040.
12. Lee, J., Sperandio, V., Frantz, D. E., Longgood, J., Camilli, A., Phillips, M. A., and A. J. Michael (2009). An Alternative Polyamine Biosynthetic Pathway Is Widespread in Bacteria and Essential for Biofilm Formation in *Vibrio cholerae.*" *The Journal of Biological Chemistry* 284(15): 9899-9907.
13. Breger, J. C., Vranish, J. N., Oh, E., Stewart, M. H., Susumu, K., Lasarte-Aragones, G., Ellis, G. A., Walper, S. A., Diaz, S. A., Hooe, S. L., Klein, W. P., Thakur, M., Ancona, M. G., Medintz, I. L. Self assembling Nanoparticle Enzyme Clusters Provide Access to Substrate Channeling in Multienzymatic Cascades. *Nature Communications* 14, 1757 (2023).

SEQUENCE LISTING

Sequence total quantity: 7
SEQ ID NO: 1                 moltype = AA   length = 493
FEATURE                      Location/Qualifiers
source                       1..493
                             mol_type = protein
                             organism = synthetic construct
SEQUENCE: 1
MNTDVRIEKD FLGEKEIPKD AYYGVQTIRA TENFPITGYR IHPELIKSLG IVKKSAALAN   60
MEVGLLDKEV GQYIVKAADE VIEGKWNDQF IVDPIQGGAG TSINMNANEV IANRALELMG   120
EEKGNYSKIS PNSHVNMSQS TNDAFPTATH IAVLSLLNQL IETTKYMQQE FMKKADEFAG   180
VIKMGRTHLQ DAVPILLGQE FEAYARVIAR DIERIANTRN NLYDINMGAT AVGTGLNADP   240
EYISIVTEHL AKFSGHPLRS AQHLVDATQN TDCYTEVSSA LKVCMINMSK IANDLRLMAS   300
GPRAGLSEIV LPARQPGSSI MPGKVNPVMP EVMNQVAFQV FGNDLTITSA SEAGQFELNV   360
MEPVLFFNLI QSISIMTNVF KSFTENCLKG IKANEERMKE YVEKSIGIIT AINPHVGYET   420
AAKLAREAYL TGESIRELCI KYGVLTEEQL NEILNPYEMT HPGIAGRKKL GPEQKLISEE   480
DLNSAVDHHH HHH                                                     493

SEQ ID NO: 2                 moltype = AA   length = 460
FEATURE                      Location/Qualifiers
source                       1..460
                             mol_type = protein
                             organism = synthetic construct
SEQUENCE: 2
MSEIVVSKFG GTSVADFDAM NRSADIVLSD ANVRLVVLSA SAGITNLLVA LAEGLEPGER   60
FEKLDAIRNI QFAILERLRY PNVIREEIER LLENITVLAE AAALATSPAL TDELVSHGEL   120
MSTLLFVEIL RERDVQAQWF DVRKVMRTND RFGAEPDIA ALAELAALQL LPRLNEGLVI    180
TQGFIGSENK GRTTTLGRGG SDYTAALLAE ALHASRVDIW TDVPGIYTTD PRVVSAAKRI   240
DEIAFAEAAE MATFGAKVLH PATLLPAVRS DIPVFVGSSK DPRAGGTLVC NKTENPPLFR   300
ALALRRNQTL LTLHSLNMLH SRGFLAEVFG ILARHNISVD LITTSEVSVA LTLDTTGSTS   360
TGDTLLTQSL LMELSALCRV EVEEGLALVA LIGNDLSKAC GVGKEVFGVL EPFNIRMICY   420
GASSHNLCFL VPGEDAEQVV QKLHSNLFEA AALEHHHHHH                         460

SEQ ID NO: 3                 moltype = AA   length = 378
FEATURE                      Location/Qualifiers
source                       1..378
                             mol_type = protein
                             organism = synthetic construct
SEQUENCE: 3
MKNVGFIGWR GMVGSVLMQR MVEERDFDAI RPVFFSTSQL GQAAPSFGGT TGTLQDAFDL   60
EALKALDIIV TCQGGDYTNE IYPKLRESGW QGYWIDAASS LRMKDDAIII LDPVNQDVIT   120
DGLNNGIRTF VGGNCTVSLM LMSLGGLFAN DLVDWVSVAT YQAASGGGAR HMRELLTQMG   180
HLYGHVADEL ATPSSAILDI ERKVTTLTRS GELPVDNFGV PLAGSLIPWI DKQLDNGQSR   240
EEWKGQAETN KILNTSSVIP VDGLCVRVGA LRCHSQAFTI KLKKDVSIPT VEELLAAHNP   300
WAKVVPNDRE ITMRELTPAA VTGTLTTPVG RLRKLNMGPE FLSAFTVGDQ LLWGAAEPLR   360
RMLRQLAAAA LEHHHHHH                                                378

SEQ ID NO: 4                 moltype = AA   length = 378
FEATURE                      Location/Qualifiers
source                       1..378
                             mol_type = protein
                             organism = synthetic construct
SEQUENCE: 4
MKNVGFIGWR GMVGSVLMQR MVEERDFDAI RPVFFSTSQL GQAAPSFGGT TGTLQDAFDL   60
EALKALDIIV TCQGGDYTNE IYPKLRESGW QGYWIDAASS LRMKDDAIII LDPVNQDVIT   120
DGLNNGIRTF VGGNCTVSLM LMSLGGLFAN DLVDWVSVAT YQAASGGGAR HMRELLTQMG   180
HLYGHVADEL ATPSSAILDI ERKVTTLTRS GELPVDNFGV PLAGSLIPWI DKQLDNGQSR   240
EEWKGQAETN KILNTSSVIP VDGLCVRVGA LRCHSQAFTI KLKKDVSIPT VEELLAAHNP   300
WAKVVPNDRE ITMRELTPAA VTGTLTTPVG RLRKLNMGPE FLSAFTVGDQ LLWGAAEPLR   360
RMLRQLAAAA LEHHHHHH                                                378

SEQ ID NO: 5                 moltype = AA   length = 521
FEATURE                      Location/Qualifiers
source                       1..521
                             mol_type = protein
                             organism = synthetic construct
SEQUENCE: 5
MVDFAEHRKA LLCNDAQSIA DYESAMGEAV KAVSAWLQNE KMYTGGSIKE LRSAISFQPS   60
KEGMGVQQSL QRMIELFLNK SLKVHHPHSL AHLHCPTMVM SQIAEVLINA TNQSMDSWDQ   120
SPAGSLMEVQ LIDWLRQKVG YGSGQAGVFT SGGTQSNLMG VLLARDWCIA KNWKDENGNP   180
WSVQRDGIPA EAMKNVKVIC SENAHFSVQK NMAMMGMGFQ SVVTVPVNEN AQMDVDALEK   240
TMAHLQAEGK VVACVVATAG TTDAGAIDPL KKIREITNKY GSWMHIDAAW GGALILSNDY   300
RAMLDGIELS DSITLDFHKH YFQSISCGAF LLKDEANYRF MHYEAEYLNS AYDEEHGVPN   360
LVSKSLQTTR RFDALKLWMT IESLGEELYG SMIDHGVKLT REVADYIKAT DGLELLVEPQ   420
FASVLFRVVP EGYPVEFIDS LNQNVADELF ARGEANIGVT KVGNVQSLKM TTLSPVVTVD   480
NVKNLLAQVL AEAERIKDAI ASGNYVPPID AAALEHHHHH H                      521

SEQ ID NO: 6                 moltype = AA   length = 972
FEATURE                      Location/Qualifiers -continued

```
source               1..972
                     mol_type = protein
                     organism = synthetic construct
SEQUENCE: 6
MSTAFEVDNH IATLFSTQVP LLDGLYDLTP DQVLLDQAAH ESEVRSYPRR IPIAIKQAYG   60
CLVEDTRGQI FLDCLAGAGT LVLGYNHPEI NQALKAQLDS GLPYQTLDIA TEAKTHFIKT  120
VKGFLPKALG EDCVIQFCGP SGADAVEAAI KLAKQTTGRN TMFAFRGAYH GMTNGTMGMM  180
GNLNTKARRT GLMSDVHFMP FPYSLRCPFG LGGDEGAKAS IRYIERLLND DEAGIMKPAA  240
IIVEPVQGEG GVIPAPAFWL RELRRICDEH GILLIFDEIQ CGVGKTGHNF APEESGIIPD  300
VLCLSKAIGG GLPMSILVIN KKHDTWRPGE HTGTFRGNQL AMVSGAKALE IIQRDNLVEH  360
ARIAGQYLRA GLEKIQSRVN CVAEVRGKGL MLGLEIKDPS GELNKFGEPK SAPQLTLAIQ  420
RAALERGLMV EKGGRDGSVI RFLPPVIISF EQLDFALRVL EEAILAAGGG KKDPEQVNQE  480
WKKHFIHTGH MGSQEFSQVM NHTTAAMKAV FEEVKAPYSG LDPKVLEEAI YAVDLDNKNA  540
SLKEVISETA ELIAKNSIMV QHPDCIAHLH TPPLMPSVVA EAIIASLNQS MDSWDQSSAA  600
TFVEQKVVDW MCEKYELGAQ ADGIFTSGGT QSNQMGLMLA RDWIADKLSG HSIQKLGLPE  660
YADKLRIVCS KKSHFTVQKS ASWMGLGEKA ILAVDALPNG TMDVTKLEAA VEQAKAEGLI  720
PFAIVGTAGT TDHGAIDDLV TIADVAEKHA LWMHVDSAYG GALILSSHKD RLNGIERAQS  780
ISVDFHKLFF QTISCGALLL KDKHNFKYLL HHADYLNREH DTLPNLVDKS ISTTKRFDAL  840
KVFMTMQNVG PKQLGAMYDH LLAQTLQVAE LVRQHQSFEL LAEPSLSTVL FRAVNEQAAD  900
LDELNKAVRL QALVRGVAVL GETIVDGKTA LKFTILNPCL TMSDFDSLLV KIEALAAELA  960
NAAALEHHHH HH                                                     972

SEQ ID NO: 7          moltype = AA  length = 188
FEATURE              Location/Qualifiers
source               1..188
                     mol_type = protein
                     organism = synthetic construct
SEQUENCE: 7
MITSAPWVLY PEIKEETRTK WIFREPKISD GDDIYSLIAD CPPLDMNSSY CNFLQSTHFS   60
KTSILVECNN DIAGFISGYQ KPDEQEVLFV WQVAVSPRYR GHGLAFRMLK ELLTREGLSN  120
VKMVETTITE DNKASWALFK KLDAMNGNSG QVSTFLDEKA HFKGKHDTEY LYRIPLKAAA  180
LEHHHHHH                                                          188
```

What is claimed is:

1. A method of conducting a cascade reaction, comprising:

providing an enzymatic cascade comprising (1) metallic quantum dots (QDs) having a plurality of enzymes bound thereto, the plurality of enzymes comprising three enzymes comprising the amino acid sequences of SEQ ID NOs: 1, 2, and 3, respectively, and (2) a fourth enzyme comprising the amino acid sequence of SEQ ID NO: 6 not bound to the QDs;

contacting the enzymatic cascade with fumarate; and allowing a reaction to proceed so that each of the plurality of enzymes acts in succession to produce 1,3-diaminopropane from the fumarate.

2. The method of claim 1, wherein the reaction is conducted in the presence of an enzyme comprising the amino acid sequence of SEQ ID NO: 7.

3. An enzymatic cascade comprising (1) metallic quantum dots (QDs) having a plurality of enzymes bound thereto, the plurality of enzymes comprising three enzymes comprising the amino acid sequences of SEQ ID NOS: 1, 2, and 3, respectively, and (2) a fourth enzyme comprising the amino acid sequence of SEQ ID NO: 6 not bound to the QDs.

4. The enzymatic cascade of claim 3 further comprising an enzyme comprising the amino acid sequence of SEQ ID NO: 7.

* * * * *